United States Patent
Togami et al.

(10) Patent No.: US 11,913,928 B2
(45) Date of Patent: Feb. 27, 2024

(54) SYSTEM FOR ESTIMATING AMOUNT OF ABSORBED CARBON DIOXIDE AND METHOD FOR ESTIMATING AMOUNT OF ABSORBED CARBON DIOXIDE

(71) Applicant: SoftBank Corp., Tokyo (JP)

(72) Inventors: Takashi Togami, Tokyo (JP); Kyosuke Yamamoto, Tokyo (JP)

(73) Assignee: SOFTBANK CORP., Tokyo (JP)

( * ) Notice: Subject to any disclaimer, the term of this patent is extended or adjusted under 35 U.S.C. 154(b) by 0 days.

(21) Appl. No.: 18/025,500

(22) PCT Filed: Sep. 29, 2021

(86) PCT No.: PCT/JP2021/035907
§ 371 (c)(1),
(2) Date: Mar. 9, 2023

(87) PCT Pub. No.: WO2022/071411
PCT Pub. Date: Apr. 7, 2022

(65) Prior Publication Data
US 2023/0288388 A1    Sep. 14, 2023

(30) Foreign Application Priority Data
Sep. 29, 2020 (JP) .................................. 2020-164026

(51) Int. Cl.
*G01N 33/00* (2006.01)
*G06Q 50/02* (2012.01)
(52) U.S. Cl.
CPC ....... *G01N 33/004* (2013.01); *G01N 33/0075* (2013.01); *G06Q 50/02* (2013.01); *G01W 2201/00* (2013.01)
(58) Field of Classification Search
CPC ...... A01G 7/00; A01G 22/00; G01N 33/0098; G01N 2021/8466
See application file for complete search history.

(56) References Cited

U.S. PATENT DOCUMENTS 4,068,405 A  *  1/1978  Campbell ............ A01G 31/042
                                                         47/65
8,082,103 B2 * 12/2011  Tanahashi ............... A01G 7/02
                                                         385/900
(Continued)

FOREIGN PATENT DOCUMENTS

JP    2005-043245 A    2/2005
JP    2010-107273 A    5/2010
(Continued)

OTHER PUBLICATIONS

John A. Gamon, "Relationships Between NDVI, Canopy Structure, and Photosynthesis in Three Californian Vegetation Types", Ecological Applications, col. 5, No. 1, Feb. 1995. (Year: 1995).*

(Continued)

*Primary Examiner* — David A. Rogers
(74) *Attorney, Agent, or Firm* — Procopio, Cory, Hargreaves & Savitch LLP

(57) ABSTRACT

The amount of carbon dioxide absorbed by plants grown in a field can more accurately be estimated based on environmental information of the field. A plurality of types of mutually-differing environmental information are measured regarding an installation field. For the plurality of types of environmental information, the correspondence relationship between each type of environmental information and a carbon dioxide ($CO_2$) absorption amount is stored. A plurality of $CO_2$ absorption amounts are acquired by referring to the respective correspondence relationship for each type of measured environmental information. The acquired plurality of $CO_2$ absorption amounts are compared with each other and the minimum value thereof is selected as the estimated value. Information regarding the selected estimated value is displayed.

7 Claims, 11 Drawing Sheets

(56) References Cited

U.S. PATENT DOCUMENTS

| | | | |
|---|---|---|---|
| 10,034,435 B2* | 7/2018 | Helene | A01G 31/06 |
| 10,473,592 B2* | 11/2019 | Kramer | G01N 21/3563 |
| 10,599,169 B2* | 3/2020 | Erickson | G05D 23/27 |
| 10,815,159 B2* | 10/2020 | Keating | C05D 1/00 |
| 11,064,659 B2* | 7/2021 | Loessl | A01G 9/00 |
| 11,089,738 B2* | 8/2021 | Wik | A01G 7/045 |
| 11,263,707 B2* | 3/2022 | Perry | A01C 21/00 |
| 11,291,165 B2* | 4/2022 | Krijn | A01G 9/249 |
| 11,536,656 B2* | 12/2022 | Ogawa | G01N 21/55 |
| 2005/0038602 A1 | 2/2005 | Uchida | |
| 2010/0286914 A1 | 11/2010 | Tanahashi | |
| 2019/0369609 A1 | 12/2019 | Takashima et al. | |

FOREIGN PATENT DOCUMENTS

| | | |
|---|---|---|
| JP | 5131282 B2 | 1/2013 |
| JP | 2016-029918 A | 3/2016 |
| JP | 2018/056071 A1 | 3/2018 |
| WO | 2009090745 A1 | 7/2009 |
| WO | 2018/021142 A1 | 2/2018 |

OTHER PUBLICATIONS

Bruce D. Cook et al., "Using Light-Use and Production Efficiency Models to Predict Photosynthesis and Net Carbon Exchange During Forest Canopy Disturbance", Ecosystems, No. 11, Nov. 13, 2007. (Year: 2007).*

International Search Report in corresponding International Application No. PCT/JP2021/035907, dated Dec. 21, 2021, in 2 pages, translation.

* cited by examiner

FIG. 5A

SETTINGS TABLE

| SENSOR ID | SENSOR POSITION | PLANT TYPE |
|---|---|---|
| S001 | 36.36, 138.895 | 1 |
| S002 | 37.21, 136.442 | 2 |
| ... | ... | ... |

ENVIRONMENTAL INFORMATION TABLE

| SENSOR ID | MEASUREMENT TIME | TEMPERATURE | RELATIVE HUMIDITY | GROUND SURFACE TEMPERATURE | SOLAR RADIATION AMOUNT | ESTIMATED VALUE |
|---|---|---|---|---|---|---|
| S001 | t1 | ... | ... | ... | ... | ... |
|  | t2 | ... | ... | ... | ... | ... |
|  | ... | ... | ... | ... | ... | ... |
| S002 | t1 | ... | ... | ... | ... | ... |
|  | t2 | ... | ... | ... | ... | ... |
|  | ... | ... | ... | ... | ... | ... |
| ... | ... | ... | ... | ... | ... | ... |

FORECAST TABLE

| SENSOR ID | FORECAST MONTH | TEMPERATURE | RELATIVE HUMIDITY | SOLAR RADIATION AMOUNT | ESTIMATED VALUE |
|---|---|---|---|---|---|
| S001 | m1 | ... | ... | ... | ... |
|  | m2 | ... | ... | ... | ... |
|  | m3 | ... | ... | ... | ... |
|  | m4 | ... | ... | ... | ... |
| S002 | m1 | ... | ... | ... | ... |
|  | m2 | ... | ... | ... | ... |
|  | m3 | ... | ... | ... | ... |
|  | m4 | ... | ... | ... | ... |
| ... | ... | ... | ... | ... | ... |

| SENSOR ID | SENSOR POSITION | PLANT TYPE |
|---|---|---|
| S001 | 36.36, 138.895 | 1 |

SETTINGS TABLE — 313

FIG. 12B

| MEASUREMENT TIME | TEMPERATURE | RELATIVE HUMIDITY | GROUND SURFACE TEMPERATURE | SOLAR RADIATION AMOUNT | ESTIMATED VALUE |
|---|---|---|---|---|---|
| t1 | ... | ... | ... | ... | ... |
| t2 | ... | ... | ... | ... | ... |
| ... | ... | ... | ... | ... | ... |

ENVIRONMENTAL INFORMATION TABLE — 314

SYSTEM FOR ESTIMATING AMOUNT OF ABSORBED CARBON DIOXIDE AND METHOD FOR ESTIMATING AMOUNT OF ABSORBED CARBON DIOXIDE

CROSS-REFERENCE TO RELATED APPLICATIONS

This application is a U.S. National Stage entry of PCT Application No. PCT/JP2021/035907, filed Sep. 29, 2021, which claims priority to Japanese Patent Application No. 2020-164026, filed Sep. 29, 2020, the contents of which are incorporated herein by reference.

FIELD

The present invention relates to a system for estimating an amount of carbon dioxide absorbed by plants based on environmental information measured in the field in which the plants are cultivated, and a carbon dioxide absorption amount estimation method.

BACKGROUND

In recent years, a system in which environmental information representing various growing environments such as air temperature, relative humidity, and solar radiation is measured by sensors installed in a field, and the carbon dioxide absorption amount absorbed by plants is estimated based on the measured environmental information is known.

For example, Patent Literature 1 describes an environment measurement device in which solar radiation intensity is calculated based on the amount of power generated by solar cells, and the calculated solar radiation intensity is converted to carbon dioxide absorption amount in light of data representing the relationship between the solar radiation intensity and a carbon dioxide absorption amount by plants prepared in advance.

CITATION LIST

Patent Literature

Patent Literature 1: Japanese Unexamined Patent Publication (Kokai) No. 2010-107273

SUMMARY

In general, various factors are involved in the carbon dioxide absorption amount of plants, and the carbon dioxide absorption amount cannot be accurately estimated only from the solar radiation amount. Thus, according to conventional estimation of carbon dioxide absorption amount based on solar radiation amount, it was not possible to accurately estimate the amount of carbon dioxide actually absorbed by plants.

The present invention aims to solve such problems of the prior art, and an object thereof is to provide a carbon dioxide absorption estimation system which can more accurately estimate the amount of carbon dioxide absorbed by plants cultivated in a field based on environmental information of the field.

In order to achieve the object described above, as one embodiment, the present invention provides a carbon dioxide absorption estimation system comprising a sensor terminal, a server, and an output device, wherein the sensor terminal comprises a sensor for measuring a plurality of mutually-differing types of environmental information related to a field provided with the sensor terminal, the server comprises a storage unit for storing correspondence relationships between respective environmental information and carbon dioxide ($CO_2$) absorption amount for the plurality of types of environmental information, a $CO_2$ absorption amount acquisition unit for acquiring a plurality of $CO_2$ absorption amounts with reference to the correspondence relationships corresponding to each type of measured environmental information, a minimum value selection unit for comparing the plurality of acquired $CO_2$ absorption amounts and selects a minimum value as an estimated value, and a transmission/reception unit for receiving the environmental information from the sensor terminal and transmits information regarding the estimated value to the output device, and the output device comprises a display unit for displaying the information related to the estimated value.

Furthermore, in order to achieve the object described above, as another embodiment, the present invention provides a carbon dioxide absorption estimation system comprising a sensor terminal, a server, and an output device, wherein the sensor terminal comprises a sensor for measuring a plurality of mutually-differing types of environmental information related to a field provided with the sensor terminal, a storage unit for storing correspondence relationships between respective environmental information and carbon dioxide ($CO_2$) absorption amount for the plurality of types of environmental information, a $CO_2$ absorption amount acquisition unit for acquiring a plurality of $CO_2$ absorption amounts with reference to the correspondence relationships corresponding to each type of measured environmental information, and a minimum value selection unit for comparing the plurality of acquired $CO_2$ absorption amounts and selects a minimum value as an estimated value, the server comprises a transmission/reception unit for receiving information regarding the environmental information from the sensor terminal and transmits the information regarding the estimated value to the output device, and the output device comprises a display unit for displaying the information related to the estimated value.

It is preferable that the sensor can measure at least one of ground surface temperature, solar radiation amount, air temperature, and relative humidity, at least one of the sensor terminal and the server has a vapor pressure deficit calculation unit for calculating a vapor pressure deficit based on the air temperature and the relative humidity, the storage unit stores a ground surface temperature-$CO_2$ absorption amount correspondence relationship between the ground surface temperature and the $CO_2$ absorption amount, a solar radiation amount-$CO_2$ absorption amount correspondence relationship between the solar radiation amount and the $CO_2$ absorption amount, and a vapor pressure deficit-$CO_2$ absorption amount correspondence relationship between the vapor pressure deficit and the $CO_2$ absorption amount as the correspondence relationships, the $CO_2$ absorption amount acquisition unit acquires a temperature-based estimated value based on the measured ground surface temperature and the ground surface temperature-$CO_2$ absorption amount correspondence relationship, a solar radiation amount-based estimated value based on the measured solar radiation amount and the solar radiation amount-$CO_2$ absorption amount correspondence relationship, and a vapor pressure deficit-based estimated value based on the vapor pressure deficit and the vapor pressure deficit-$CO_2$ absorption amount correspondence relationship as the plurality of $CO_2$ absorption amounts, and the minimum value selection unit selects whichever is least among the temperature-based estimated value, the solar radiation amount-based estimated value, and the vapor pressure deficit-based estimated value as the estimated value.

It is preferable that the storage unit stores a correspondence relationship defined for each type of plant for the ground surface temperature-$CO_2$ absorption amount correspondence relationship and the solar radiation amount-$CO_2$ absorption amount correspondence relationship, and the $CO_2$ absorption amount acquisition unit references the correspondence relationships in accordance with the plant cultivated in the field where the sensor is installed.

It is preferable that the sensor measures the plurality of types of environmental information at predetermined time intervals, the $CO_2$ absorption amount acquisition units acquires the plurality of $CO_2$ absorption amounts each time the plurality of types of environmental information are measured, and the minimum value selection unit selects the estimated value each time the plurality of $CO_2$ absorption amounts are acquired.

It is preferable that there further be provided an integration unit for integrating the estimated values selected within a predetermined interval.

As another embodiment, the present invention provides a carbon dioxide absorption amount estimation method, comprising the steps of: measuring, by a sensor terminal, a plurality of types of mutually-differing environmental information related to a field provided with the sensor terminal using a sensor, receiving, by a server, the plurality of types of environmental information from the sensor terminal, referring, by the server, to a correspondence relationship between each of the plurality of types of environmental information and carbon dioxide ($CO_2$) absorption amounts, which are stored in advance in a storage device, for each of the received environmental information to acquire a plurality of $CO_2$ absorption amounts, comparing, by the server, the acquired plurality of $CO_2$ absorption amounts with each other and selects a minimum value as an estimated value, transmitting, by the server, information regarding the estimated value to an output device, and displaying, by the output device, the information regarding the estimated value.

As another embodiment, the present invention provides a carbon dioxide absorption amount estimation method, comprising the steps of: acquiring solar radiation information regarding an amount of solar radiation emitted onto a field, temperature information regarding a temperature of the field, and humidity information regarding a humidity of the field, calculating vapor pressure deficit information of the field based on the temperature information and the humidity information, calculating a temperature-based estimated value based on the temperature information, a solar radiation amount-based estimated value based on the solar radiation information, and a vapor pressure deficit-based estimated value based on the vapor pressure deficit information, which are estimated values of an absorption amount of carbon dioxide per unit time of the field, and selecting a minimum value obtained by comparing the temperature-based estimated value, the solar radiation amount-based estimated value, and the vapor pressure deficit-based estimated value with each other as an estimated value of the absorption amount of carbon dioxide of the field.

The carbon dioxide absorption estimation system according to the present invention can more accurately estimate an amount of carbon dioxide absorbed by plants cultivated in a field based on environmental information of the field.

BRIEF DESCRIPTION OF DRAWINGS

FIG. 5A is a view showing an example of a data structure of a settings table representing correspondence relationships between sensor IDs, sensor positions, and plant types.

FIG. 5B is a view showing an example of a data structure of an environmental information table representing the correspondence relationships between measurement time, sensor IDs, environmental information, and estimated values.

FIG. 5C is a view showing an example of a data structure of a forecast table showing correspondence relationships between sensor IDs and predicted values.

FIG. 12A is a view showing an example of a data structure of a settings table representing correspondence relationships between sensor IDs, sensor positions, and plants types.

FIG. 12B is a view showing an example of a data structure of an environmental information table representing the correspondence relationships between measurement time, environmental information, and estimated values.

DESCRIPTION OF EMBODIMENTS

Various embodiments of the present invention will be described below with reference to the drawings. However, the scope of the present invention is not limited to such embodiments, but rather extends to the invention recited in the claims and equivalents thereof.

1. Carbon Dioxide Absorption Estimation System 1

1.1 Overview of Carbon Dioxide Absorption Estimation System 1

Figure 1:
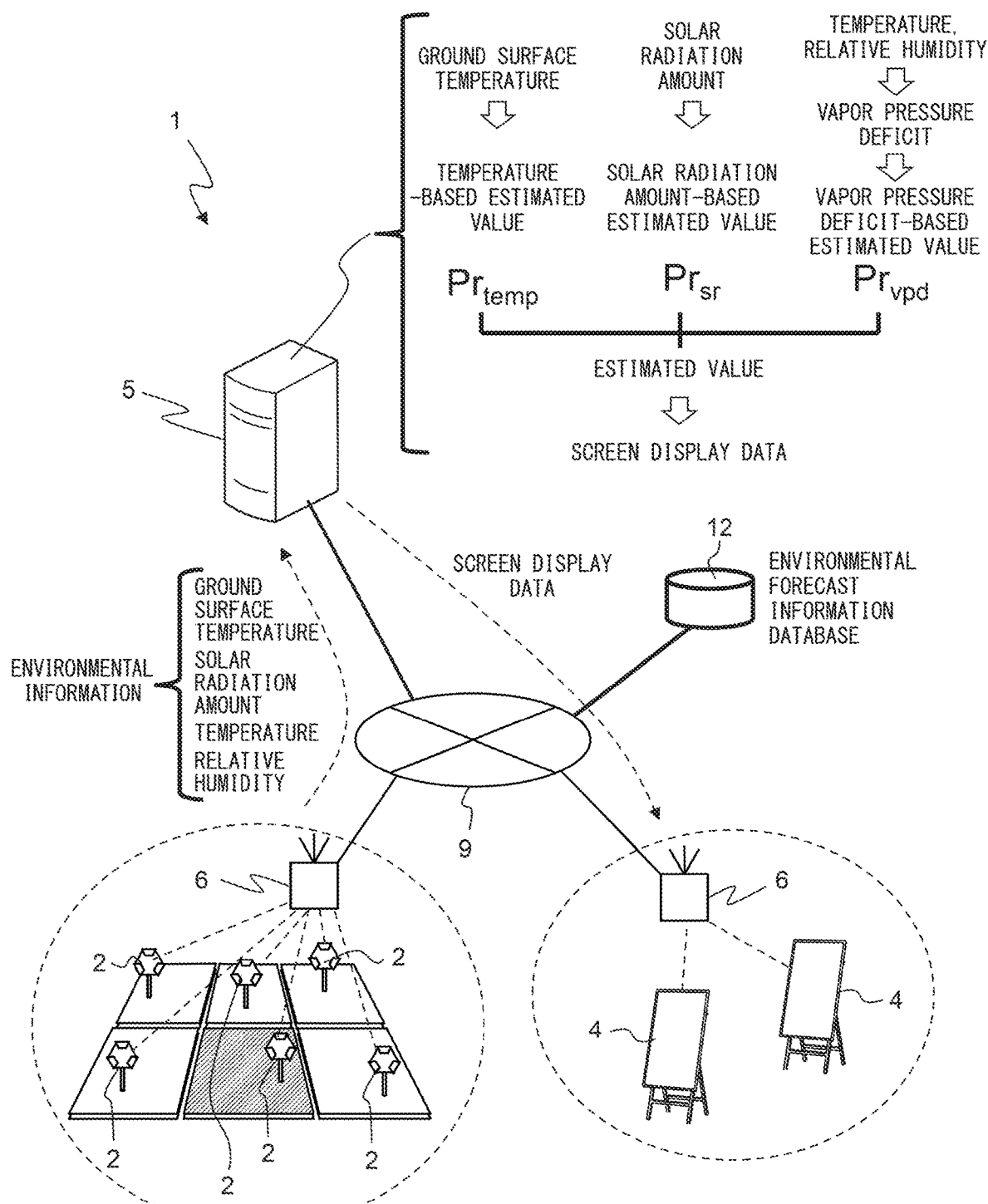
FIG. 1 is a schematic view detailing an overview of a carbon dioxide absorption estimation system according to a first embodiment of the present invention.

FIG. 1 is a schematic view detailing an overview of the carbon dioxide absorption estimation system 1. The carbon dioxide absorption estimation system 1 comprises one or more of sensor terminals 2, a display terminal 4, a server 5, a base station 6, and an environmental forecast information database 12. The sensor terminal 2 and the server 5 as well as the server 5 and the display terminal 4 are interconnected via the base station 6 and the Internet 9. The base station 6 serves as a connection between the sensor terminal 2 and the Internet 9 and serves as a connection between the display terminal 4 and the Internet 9.

A sensor terminal 2 is installed in each of a plurality of fields and transmits environmental information of the field provided with the sensor terminal to the server 5. The server 5 estimates the carbon dioxide absorption amount of each field based on the environmental information, and generates screen display data based on the estimated value. The display terminal 4 displays the screen display data. The environmental forecast information database 12 is a database provided by the Japan Meteorological Agency or an operator who performs weather forecasting. The environmental forecast information database 12 stores environmental forecast information including forecast values for the temperature, relative humidity, and solar radiation amount of the fields where the sensor terminals 2 are installed up to 8 days in advance, and the average yearly values for each day for at least 3 months thereafter, and provides the environmental forecast information to the server 5 via the Internet 9. The display terminal 4 and the base station 6 are connected to each other by wireless communication. The display terminal 4 and the server 5 are connected to each other via the base station 6 and the Internet 9.

In each field, for example, one of two types of sod C3, C4 is cultivated. Hereinafter, the plant type of sod C3 is defined as 1, and the plant type of sod C4 is defined as 2. Sod C3 is cold climate sod, and the suitable temperature for growth is 15 to 20° C. Sod C3 grows even at low temperatures of approximately 5° C. and in warm areas it can remain green even in winter. However, sod C3 easily withers at high temperatures in summer. Sod C4 is a warm climate sod, and the suitable temperature for growth is 25 to 35° C. Though sod C4 grows well even at high temperatures in summer, it is dormant at low temperatures in late autumn and withers above ground. Sod C4 tends to be late to green in early spring.

In the carbon dioxide absorption estimation system 1, the sensor terminal 2 installed in each field measures a plurality of different types of environmental information at regular intervals. The server 5 determines the estimated value of carbon dioxide that the plants cultivated in the field where the sensor terminal 2 is installed absorb within a certain period of time based on the environmental information measured by the sensor terminal 2, and generates screen display data based on the calculated estimated value. The display terminal 4 is a terminal for performing network-compatible digital signage, and displays the screen display data generated by the server 5.

First, sensor units connected to the sensor terminal 2 measure the air temperature, relative humidity, ground surface temperature, and solar radiation amount in the field where the sensor terminal 2 is installed at a predetermined interval, which are then transmitted to the server 5 via the base station 6 and the Internet 9 in association with the sensor ID representing the sensor terminal 2. The predetermined interval is, for example, 10 minutes.

The correspondence relationship between the factor used as the basis for calculating the estimated value of the $CO_2$ absorption amount and the actual $CO_2$ absorption amount, i.e., the factor-$CO_2$ absorption amount correspondence relationship, is stored in advance in the storage device of the server 5. The server 5 stores the correspondence relationship between each of the three factors of ground surface temperature, solar radiation amount, and vapor pressure deficit and the $CO_2$ absorption amount. The ground surface temperature-$CO_2$ absorption amount correspondence relationship data indicates, for each type of plant, the correspondence relationship between the ground surface temperature T of the field in which the plants of that type are cultivated and the $CO_2$ absorption amount $Pr_{temp}$ of the plants. The solar radiation amount-$CO_2$ absorption amount correspondence relationship data indicates, for each type of plant, the correspondence relationship between the solar radiation amount R of the field in which the plants of that type are cultivated and the $CO_2$ absorption amount $Pr_{sr}$ of the plants. The vapor pressure deficit-$CO_2$ absorption amount correspondence relationship data indicates the correspondence relationship between the vapor pressure deficit D of the field in which the plants are cultivated and the $CO_2$ absorption amount $Pr_{vpd}$ of the plants.

The server 5 determines the type of plants cultivated in the field based on the received sensor ID, converts the ground surface temperature received together with the sensor ID to the ground surface temperature-$CO_2$ absorption amount correspondence relationship data of the determined plant type to determine the temperature-based estimated value $Pr_{temp}$. The server 5 converts the solar radiation amount received together with the determined sensor ID to the solar radiation amount-$CO_2$ absorption amount correspondence relationship data of the determined plant type to determine the solar radiation-based estimated value $Pr_{sr}$. The server 5 determines the vapor pressure deficit D based on the received air temperature and relative humidity together with the determined sensor ID, and converts the vapor pressure deficit D to the vapor pressure deficit-$CO_2$ absorption amount correspondence relationship data of the determined plant type to determine the vapor pressure deficit-based estimated value $Pr_{vpd}$.

Next, the server 5 compares the three obtained estimated values $Pr_{temp}$, $Pr_{sr}$, and $Pr_{vpd}$ with each other and selects the minimum value as the estimated value. By applying Liebig's Law of the Minimum to the three estimated values, the minimum of the photosynthetic rate is selected. The server 5 generates screen display data based on the obtained estimated value, and transmits the generated screen display data to the display terminal 4 via the Internet 9 and the base station 6.

Next, the display terminal 4 receives the screen display data transmitted from the server 5 and displays the screen display data.

As described above, the carbon dioxide absorption estimation system 1 obtains three $CO_2$ absorption amounts based on the ground surface temperature, the solar radiation amount, and the vapor pressure deficit, and uses the minimum value thereamong as the estimated value. Thus, the $CO_2$ absorption amount can be estimated with higher accuracy as compared to estimation of the $CO_2$ absorption amount based on a single environmental factor (for example, solar radiation amount).

German chemist Eustus von Liebig proposed that the growth rate and yield of plants are limited only by the required nutrient of the least quantity (Liebig's Law of the Minimum). The present invention applies Liebig's Law of the Minimum to the estimation of the $CO_2$ absorption amount.

Specifically, in the present invention, attention is focused on the mutually-differing first, second, ..., n-th (where n is a natural number of 2 or more) factors which significantly impact the $CO_2$ absorption amount of plants. The measurement value related to the first factor is the measurement value M1, the measurement value related to the second factor is the measurement value M2, . . . , the measurement value related to the n-th factor is the measurement value Mn, the estimated value of the $CO_2$ absorption amount based on the measurement value M1 is the estimated value P1, the estimated value of the $CO_2$ absorption amount based on the measurement value M2 is the estimated value P2, . . . , and the estimated value of the $CO_2$ absorption amount based on the measurement value Mn is the estimated value Pn. At this time, in the present invention, Liebig's Law of the Minimum is applied to the estimated values P1, P2, . . . , Pn, and the one having the minimum value is adopted as the estimated value.

When estimating the $CO_2$ absorption amount based on a single factor, there is a risk that an estimated value which cannot be achieved due to the influence of other factors is obtained. Conversely, as described above, when adopting the minimum value among the plurality of estimated values mutually differing in the factor used as the basis for the calculation as the estimated value, the possibility of obtaining an estimated value based on factors which have a decisive influence on the $CO_2$ absorption amount of the plants at that time can be increased. As a result, a more accurate estimated value can be obtained. In the present disclosure, as an example of a combination of factors to which attention is paid when estimating the $CO_2$ absorption amount, the combination of the ground surface temperature, solar radiation amount, and vapor pressure deficit described above is used.

By estimating the $CO_2$ absorption amount by means of the server 5 for each measurement by the sensor terminal 2, it becomes possible to estimate the $CO_2$ absorption amount at short time intervals of, for example, 10 to 30 minutes or so. Thus, an estimated value which reflects actual environment changes of the field can be obtained as compared to estimating the $CO_2$ absorption amount based on estimated values obtained once daily, such as the Mesh Agro-Meteorological data provided by the NARO.

1.2. Configuration of Sensor Terminal 2

Figure 2:
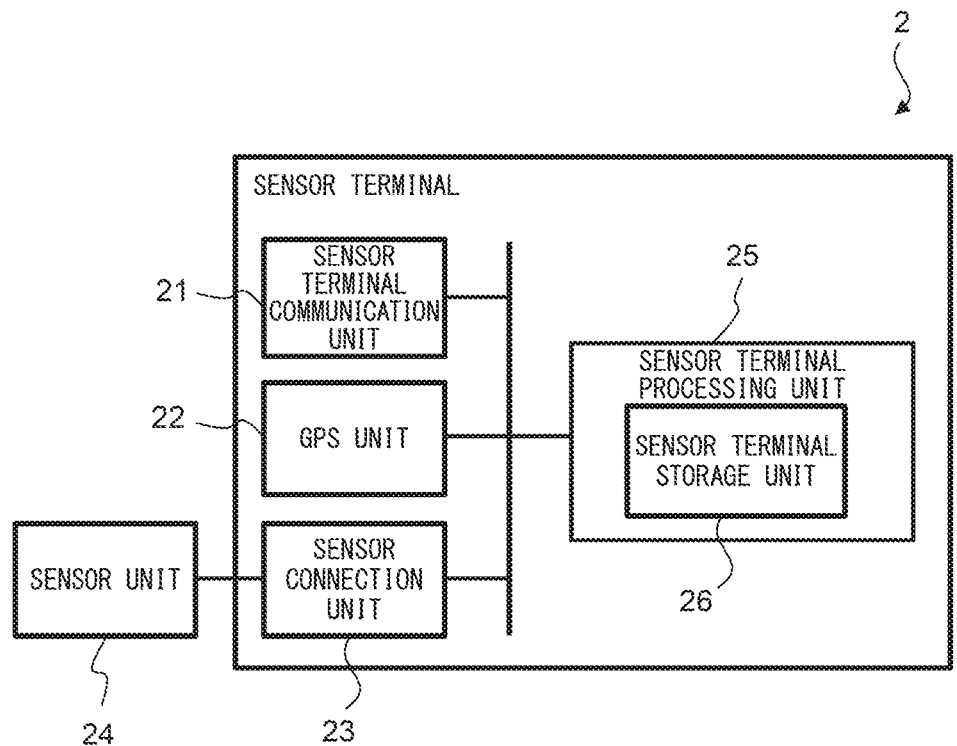
FIG. 2 is a view showing an example of a schematic configuration of a sensor terminal.

FIG. 2 is a view showing an example of the schematic configuration of the sensor terminal 2.

The sensor terminal 2 acquires environmental information representing the measured environmental factors, and transmits the environmental information. Thus, the sensor terminal 2 comprises a sensor terminal communication unit 21, a GPS (Global Positioning System) unit 22, a sensor connection unit 23, a sensor unit 24, a sensor terminal processing unit 25, and a sensor terminal storage unit 26.

The sensor terminal communication unit 21 has a communication interface circuit including an antenna with the sensitive band of which is mainly the 2.4 GHz band, 5 GHz band, etc., and performs wireless communication with the wireless LAN (Local Area Network) base station 6 based on the IEEE (The Institute of Electrical and Electronics Engineers, Inc.) 802.11 standard wireless communication method. The frequency band of the sensor terminal communication unit 21 is not limited to the frequency bands described above. The sensor terminal communication unit 21 transmits environmental information supplied from the sensor terminal processing unit 25 to the base station 6.

The GPS unit 22 has a GPS circuit including an antenna mainly sensitive to the 1.5 GHz band, and receives a GPS signal from a GPS satellite (not illustrated). The GPS unit 22 decodes the GPS signal and acquires time information. Next, the GPS unit 22 calculates the pseudo-range from the GPS satellite to the sensor terminal 2 based on the time information, and detects the position (latitude, longitude, altitude, etc.) where the sensor terminal 2 is present by solving simultaneous equations obtained by substituting the pseudo-range. The GPS unit 22 then associates the position information representing the detected position with the acquired time information, and periodically outputs the information to the sensor terminal processing unit 25.

The sensor connection unit 23 includes a sensor terminal which is connected with the sensor unit 24, and is connected with the sensor unit 24 for measuring one or more of types of environmental factors.

The sensor unit 24 has an air temperature sensor for measuring air temperature, a relative humidity sensor for measuring relative humidity, a ground surface temperature sensor for measuring ground surface temperature, and a solar radiation sensor for measuring solar radiation amount. The air temperature is the air temperature at 1.25 to 2.0 m above the ground in the field where the sensor terminal 2 is installed, and the unit thereof is Celsius (° C.). The relative humidity is the ratio of the amount of water vapor in the field where the sensor terminal 2 is installed and the amount of saturated water vapor at the air temperature at that time expressed as a percentage. The ground surface temperature is the temperature of the ground surface in the field where the sensor terminal 2 is installed, and the unit thereof is Celsius (° C.). The solar radiation amount is the solar radiation amount in the field where the sensor terminal 2 is installed, and the unit thereof is watts per square meter ($W/m^2$).

The sensor terminal processing unit 25 has one or more of processors and peripheral circuits thereof. The sensor terminal processing unit 25 comprehensively controls the overall operations of the sensor terminal 2 and includes, for example, a CPU (Central Processing Unit). The sensor terminal processing unit 25 controls the operations of the sensor terminal communication unit 21, the GPS unit 22, and the sensor unit 24 so that the various processes of the sensor terminal 2 are executed in an appropriate procedure according to the programs, etc., stored in the sensor terminal storage unit 26. The sensor terminal processing unit 25 performs processing based on the programs (driver program, operating system program, etc.) stored in the sensor terminal storage unit 26.

The sensor terminal storage unit 26 has, for example, a semiconductor memory. The sensor terminal storage unit 26 stores the sensor ID, which is identification information for identifying the sensor terminal 2, driver programs, operating system programs, data, etc., used for processing in the sensor terminal processing unit 25. For example, the sensor terminal storage unit 26 stores, as driver programs, a wireless communication device driver program that controls the sensor terminal communication unit 21, a GPS driver program that controls the GPS unit 22, a sensor driver program that controls the sensor unit 24, etc. The sensor terminal storage unit 26 also stores, as operating system programs, a wireless control program for executing wireless communication based on the IEEE 802.11 standard wireless communication method. The sensor terminal storage unit 26 also stores environmental information representing the environmental factors measured by the sensor unit 24 as data.

1.3. Configuration of Display Terminal 4

Figure 3:
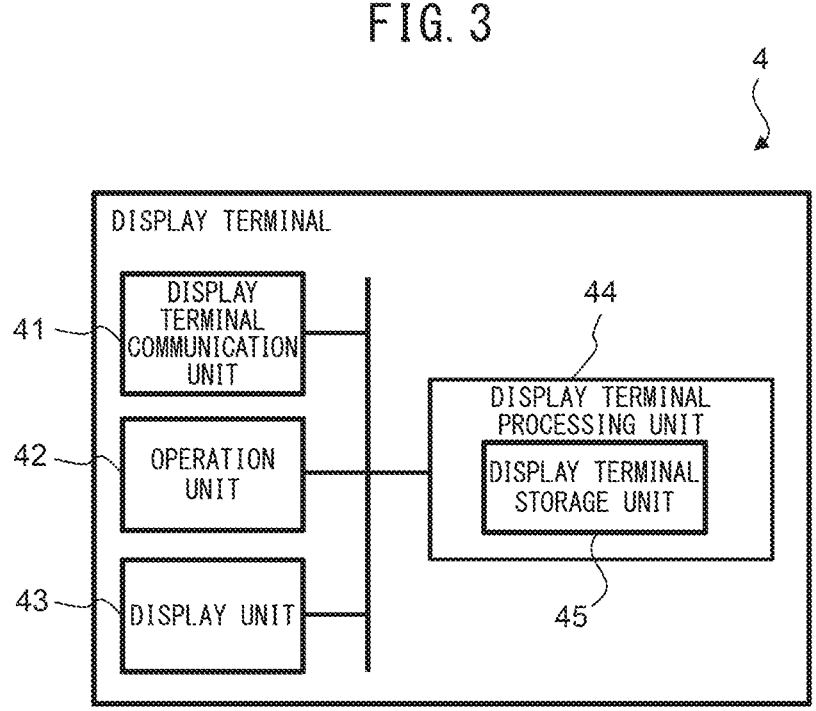
FIG. 3 is a view showing an example of a schematic configuration of a display terminal.

FIG. 3 is a view showing an example of the schematic configuration of the display terminal 4.

The display terminal 4 is an example of an output device having a display unit for displaying information regarding the estimated values. The display terminal 4 is a terminal which functions as digital signage, and displays the screen display data generated by the server 5. Thus, the display terminal 4 comprises a display terminal communication unit 41, an operation unit 42, a display unit 43, a display terminal processing unit 44, and a display terminal storage unit 45.

The sensor terminal communication unit 41 has a communication interface circuit including an antenna with the sensitive band of which is mainly the 2.4 GHz band, 5 GHz band, etc., and performs wireless communication with wireless LAN (Local Area Network) access points (not illustrated) based on the IEEE (The Institute of Electrical and Electronics Engineers, Inc.) 802.11 standard wireless communication method. The frequency band of the sensor terminal communication unit 41 is not limited to the frequency bands described above. The display terminal communication unit 41 provides the data received from the base station 6 to the display terminal processing unit 44 and transmits the data supplied from the display terminal processing unit 44 to the base station 6.

The operation unit 42 may be any type of device as long as it is capable of operating the display terminal 4, for example, a touch panel input device or a keypad. The administrator of the display terminal 4 can use this device to enter letters, numbers, etc. The operation unit 42, when operated by the administrator, generates signals corresponding to the operations. The generated signals are input to the display terminal processing unit 44 as instructions from the administrator of the display terminal 4.

The display unit 43 is an example of a display unit for displaying information regarding the estimated values. The display unit 43 may be any type of device as long as it can output video, images, etc., for example, a touch panel display device, a liquid crystal display, an organic EL (Electro-Luminescence) display, etc. The display unit 43 displays videos in accordance with video data, images in accordance with image data, etc., supplied from the display terminal processing unit 44.

The display terminal processing unit 44 has one or more of processors and peripheral circuits thereof. The display terminal processing unit 44 controls the overall operations of the display terminal 4 and has, for example, a CPU (Central Processing Unit). The display terminal processing unit 44 controls the operations of the display terminal communication unit 41, the display unit 43, etc., so that the various processes of the display terminal 4 are executed according to appropriate procedures in accordance with the programs stored in the display terminal storage unit 45 and the outputs from the operations of the operation unit 42. The display terminal processing unit 44 performs processing based on the programs (driver programs, operating system programs, application programs, etc.) stored in the display terminal storage unit 45. The display terminal processing unit 44 can execute a plurality of programs (application programs, etc.) in parallel.

The display terminal storage unit 45 has, for example, a semiconductor memory. The display terminal storage unit 45 stores driver programs, operating system programs, application programs, data, etc., used in the processing by the display terminal processing unit 44. For example, the display terminal storage unit 45 stores, as driver programs, a wireless LAN communication device driver program which controls the display terminal communication unit 41, an input device driver program which controls the operation unit 42, an output device driver program which controls the display unit 43, etc. The display terminal storage unit 45 also stores, as operating system programs, a connection control program for executing the IEEE 802.11 standard wireless communication system, etc. The display terminal storage unit 45 also stores a program for executing digital signage processing for displaying the screen display data received from the server 5 on the display unit 43. The computer programs may be installed on the display terminal storage unit 45 from a computer-readable portable storage medium such as CD-ROM (compact disk read only memory), a DVD-ROM (digital versatile disk read only memory), etc., using a known setup program.

1.4. Configuration of Server 5

Figure 4:
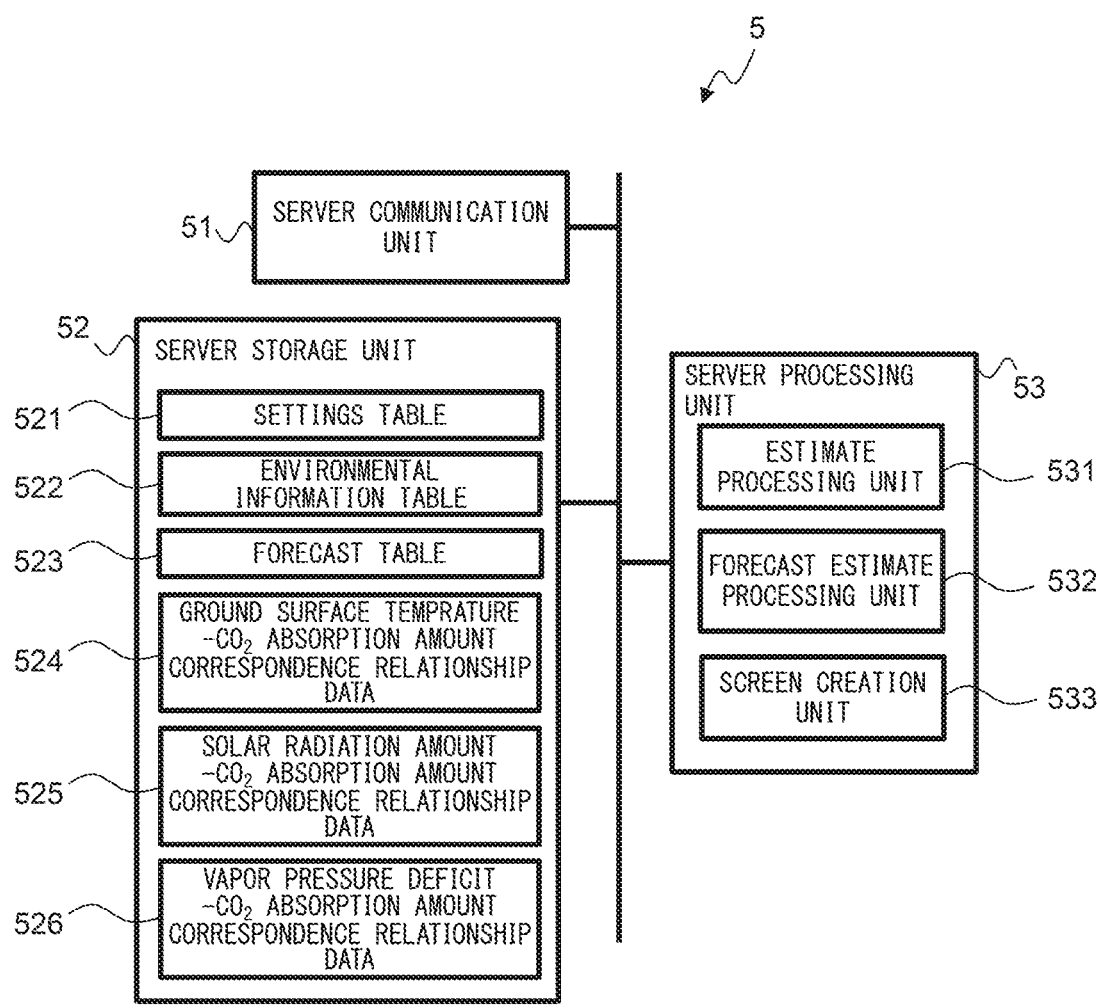
FIG. 4 is a view showing an example of a schematic configuration of a server.
Figure 6A:
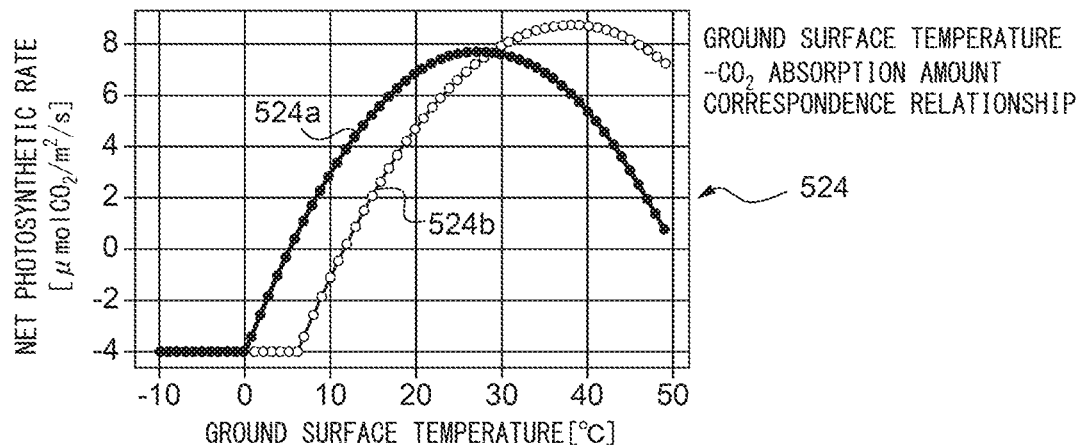
FIG. 6A is an example of data showing the correspondence relationships between ground surface temperature and $CO_2$ absorption amount for various types of plants.
Figure 6B:
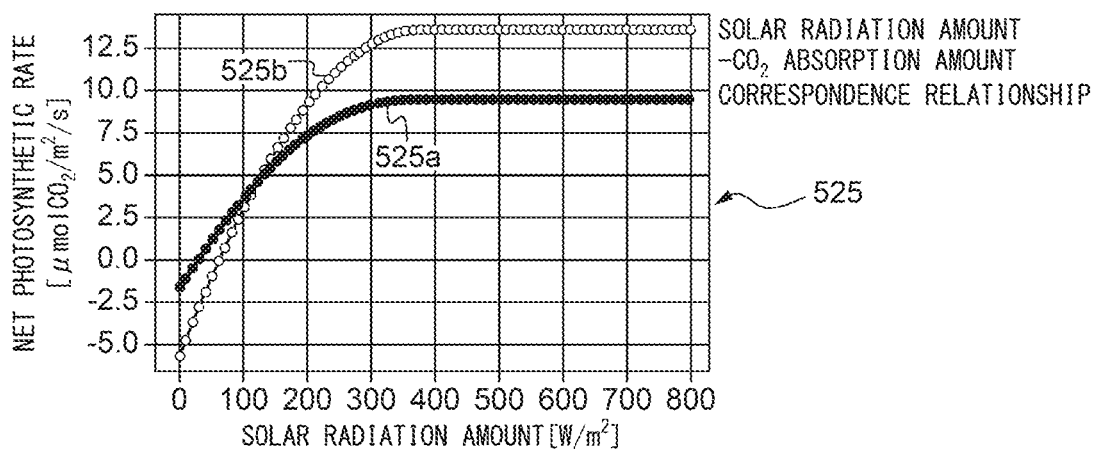
FIG. 6B is an example of data showing the correspondence relationships between solar radiation amount and $CO_2$ absorption amount for various types of plants.
Figure 6C:
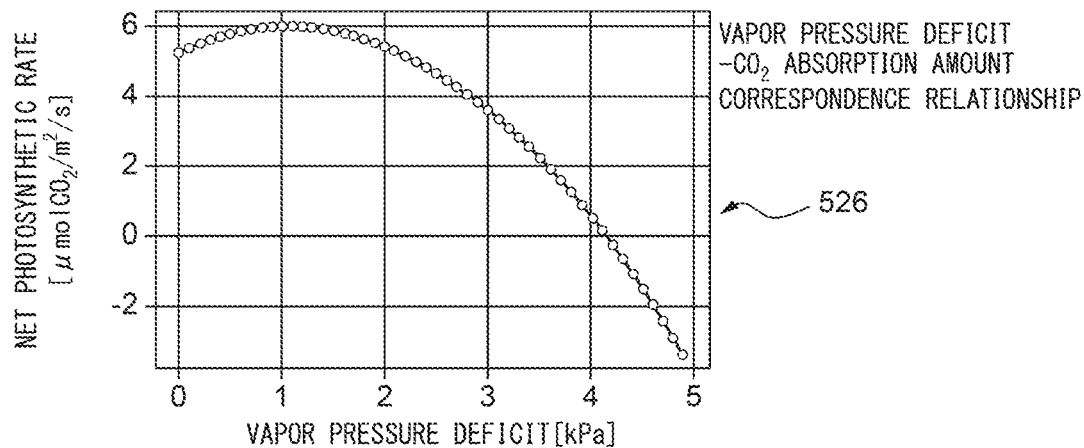
FIG. 6C is an example of data showing the correspondence relationships between vapor pressure deficit and $CO_2$ absorption amount common between type 1 and type 2 plants.

FIG. 4 is a view showing an example of the schematic configuration of the server 5. FIG. 5A is a view showing an example of the data structure of a settings table representing the correspondence relationships of sensor IDs, sensor positions, and plant types, FIG. 5B is a view showing an example of the data structure of an environmental information table representing the correspondence relationship between measurement time, sensor ID, environmental information, and estimated value, and FIG. 5C is a view showing an example of the data structure of a forecast table representing the correspondence relationships between sensor ID and predicted values. FIG. 6A is an example of data representing the correspondence relationship between ground surface temperature and $CO_2$ absorption amount for each type of plant, FIG. 6B is an example of data representing the correspondence relationship between the solar radiation amount and the $CO_2$ absorption amount for each type of plant, and FIG. 6C is an example of data representing the correspondence relationship between the vapor pressure deficit and the $CO_2$ absorption amount common between plant types 1 and 2.

When the server 5 receives environmental information from the sensor terminal 2, it accumulates and manages the environmental information and transmits screen display data to the display terminal 4. The server 5 comprises a server communication unit 51, a server storage unit 52, and a server processing unit 53.

The server communication unit 51 has a communication interface circuit for connecting the server 5 to the Internet 9. The server communication unit 51 receives data transmitted from the sensor terminal 2 and data transmitted from the display terminal 4 and supplies each type of received data to the server processing unit 53.

The server storage unit 52 is an example of a storage unit for storing the correspondence relationships between environmental information and carbon dioxide ($CO_2$) absorption amounts for a plurality of types of environmental information. The server storage unit 52 has, for example, at least one of a semiconductor memory, a magnetic disk device, and an optical disk device. The server storage unit 52 stores driver programs, operating system programs, application programs, data, etc., used for processing by the server processing unit 53. For example, the server storage unit 52 stores a communication device driver program for controlling the server communication unit 51 as a driver program. The computer program may be installed in the server storage unit 52 from a computer-readable portable recording medium such as a CD-ROM, DVD-ROM, etc., using a known setup program or the like.

The server storage unit 52 stores, as data, a settings table 521 shown in FIG. 5A, an environmental information table 522 shown in FIG. 5B, a forecast table 523 shown in FIG. 5C, ground surface temperature-$CO_2$ absorption amount correspondence relationship data 524 shown in FIG. 6A, solar radiation amount-$CO_2$ absorption amount correspondence relationship data 525 shown in FIG. 6B, vapor pressure deficit-$CO_2$ absorption amount correspondence relationship data 526 shown in FIG. 6C, and various image data related to screen display. Further, the server storage unit 52 may temporarily store temporary data related to predetermined processing.

The settings table 521 stores sensor IDs, sensor positions, and plant types in association with each other. The sensor ID is identification information of the sensor terminal 2. The sensor position is the latitude and longitude representing the position where the sensor terminal 2 is installed. The plant type represents the type of plant cultivated in the field where the sensor terminal 2 is installed. When the plant type is 1, it indicates that the cold region sod (C3 plant) is cultivated in the field where the sensor terminal 2 is installed. When the plant type is 2, it indicates that a warm climate sod (C4 plant) is cultivated in the field where the sensor terminal 2 is installed. Each value of the settings table 521 is set in advance by an administrator or the like of the server 5 using an input device such as a keyboard (not illustrated) of the server 5.

The environmental information table 522 stores the sensor ID, measurement time, air temperature, relative humidity, ground surface temperature, solar radiation amount, and estimated value in association with each other. The measurement time is the time when the sensor unit 24 of the sensor terminal 2 measured the environmental information. Air temperature, relative humidity, ground surface temperature, and solar radiation amount are examples of a plurality of mutually-differing types of environmental information measured by the sensor unit 24 of the sensor terminal 2. The minimum estimated value is a value obtained by executing the estimate processing described later based on the corresponding plant type, air temperature, air temperature, relative humidity, ground surface temperature, and solar radiation amount.

For example, the air temperature, relative humidity, ground surface temperature, and solar radiation amount measured by sensor terminal 2 having sensor ID=S001 at measurement time t1 are stored in the first-row record of the environmental information table shown in FIG. 5B, and the estimated values obtained by estimated processing based on these are further stored.

The forecast table 523 stores sensor ID, forecast date, air temperature, relative humidity, solar radiation amount, and estimated value in association with each other. The forecast date indicates the date on which the forecast is to be made. Air temperature, relative humidity and solar radiation amount indicate respective predicted values. Regarding the estimated values, the estimated values obtained by estimation processing based on predicted values of air temperature, relative humidity, and solar radiation amount are stored.

The ground surface temperature-$CO_2$ absorption amount correspondence relationship data 524 is data in which, for each of the plants of plant type 1 (cold region sod C3) and the plants of plant type 2 (warm region sod C4), the relationship between the ground surface temperature T of a field where each type of plants are cultivated and the amount of carbon dioxide $Pr_{temp}$ absorbed by the plants in that field is determined based on past performance and experimentation. Curve 524a represents the correspondence relationship for plant type 1, and curve 524b represents the correspondence relationship for plant type 2. The ground surface temperature-$CO_2$ absorption amount correspondence relationship data 524 is graphed in FIG. 6A but is stored as a table in the server storage unit 52.

The solar radiation amount-$CO_2$ absorption amount correspondence relationship data 525 is data in which, for each plant of plant type 1 and plant of plant type 2, the relationship between the amount of solar radiation R in a field where each type of plants are cultivated and the amount of carbon dioxide $Pr_{sr}$ absorbed by the plants in that field is determined based on past performance and experimentation. Curve 525a represents the correspondence relationship of plant type 1, and curve 525b represents the correspondence relationship of plant type 2. The solar radiation amount-$CO_2$ absorption amount correspondence relationship data 525 is graphed in FIG. 6B but is stored as a table in the server storage unit 52.

The vapor pressure deficit-$CO_2$ absorption amount correspondence relationship data 526 is data in which the relationship between the vapor pressure deficit D of a field where plants are cultivated and the amount of carbon dioxide $Pr_{vpd}$ absorbed by the plants in that field is determined in advance based on past performance and experimentation. The vapor pressure deficit-$CO_2$ absorption amount correspondence relationship data 526 is applied to both the plants of plant type 1 and the plants of plant type 2, unlike the ground surface temperature-$CO_2$ absorption amount correspondence relationship data 524 and the solar radiation amount-$CO_2$ absorption amount correspondence relationship data 525. The vapor pressure deficit-$CO_2$ absorption amount correspondence relationship data 526 is graphed in FIG. 6C but is stored as a table in the server storage unit 52.

Returning to FIG. 4, the server processing unit 53 has one or more of processors and peripheral circuits thereof. The server processing unit 53 controls the overall operations of the server 5, and is, for example, a CPU. The server processing unit 53 controls the operations of the server communication unit 51, etc., so that the various processes of the server 5 are executed according to appropriate procedures in accordance with the programs and the like stored in the server storage unit 52. The server processing unit 53 executes processing based on the programs (driver program, operating system program, application program, etc.) stored in the server storage unit 52. The server processing unit 53 can execute a plurality of programs (application programs, etc.) in parallel.

The server processing unit 53 comprises an estimate processing unit 531, a forecast estimate processing unit 532, and a screen creation unit 533. The estimate processing unit 531 is an example of a $CO_2$ absorption amount acquisition unit for acquiring a plurality of $CO_2$ absorption amounts by referring to correspondence relationships corresponding to each type of measured environmental information. The estimate processing unit 531 is an example of a minimum value selection unit for comparing the plurality of acquired $CO_2$ absorption amounts and selects the minimum value there among as the estimated value. The estimate processing unit 531 is an example of a vapor pressure deficit calculation unit which calculates the vapor pressure deficit based on air temperature and relative humidity. The screen creation unit 533 is an example of an integration unit which integrates the estimated values selected within a predetermined period. Each unit of the server processing unit 53 is a functional module implemented by a program executed by the processor of the server processing unit 53. Alternatively, each unit of the server processing unit 53 may be implemented in the server 5 as an independent integrated circuit, microprocessor, or firmware.

1.5. Operations of Carbon Dioxide Absorption Estimation System 1

In the sensor terminal 2, the sensor terminal processing unit 25 measures the air temperature, relative humidity, ground surface temperature, and solar radiation amount of the field where the sensor terminal 2 is installed at regular intervals (e.g., 10 minutes) using the sensor unit 24, and acquires the time at which these measurements are made as the measurement time using the GPS unit 22. The sensor terminal processing unit 25 associates the sensor ID read from the sensor terminal storage unit 26, the environmental information including measured air temperature, relative humidity, ground surface temperature, and solar radiation amount, and the measurement time at which the environmental information was measured with each other, and transmits them to the server 5 via the base station 6 and the Internet 9 using the sensor terminal communication unit 21.

Figure 7:
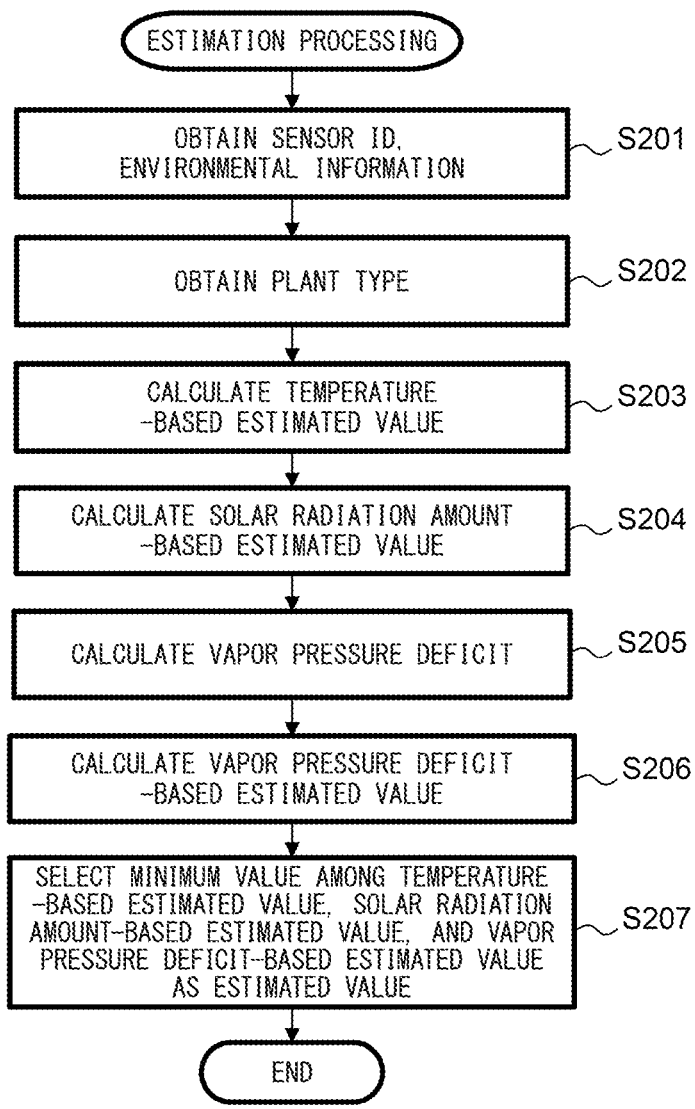
FIG. 7 is a flowchart showing an example of estimation processing.

FIG. 7 is a flow chart showing an example of estimation processing by the estimate processing unit 531. Every time the server 5 receives environmental information received by the server communication unit 51, the server processing unit 53 executes the following estimation processing.

When the estimate processing unit 531 acquires the environmental information (step S201), it refers to the settings table 521 and acquires the plant type corresponding to the sensor ID included in the environmental information (step S202).

Next, the estimate processing unit 531 refers to the data corresponding to the plant type acquired in step S202 among the ground surface temperature-$CO_2$ absorption amount correspondence relationship data 524, and calculates the temperature-based estimated value $Pr_{temp}$ corresponding to the ground surface temperature included in the environmental information (step S203).

Next, the estimate processing unit 531 refers to the data corresponding to the plant type acquired in step S202 among the solar radiation amount-$CO_2$ absorption amount correspondence relationship data 525, and calculates the solar radiation amount-based estimated value $Pr_{sr}$ corresponding to the solar radiation amount included in the environmental information (step S204).

Next, the estimate processing unit 531 converts the air temperature and relative humidity included in the environmental information with the following formula (1) to determine the vapor pressure deficit D (step S205). In formula (1), the unit of temperature T is Celsius (° C.), the unit of relative humidity R is percent (%), and the unit of vapor pressure deficit D is hectopascal (hPa).

[Math 1]

$$\left. \begin{array}{l} eT = 6.1078 \times 10^{\left(7.5 \times \frac{T}{T+237.3}\right)} \\ D = eT \times \frac{1-R}{100.0} \end{array} \right\} \quad (1)$$

Next, the estimate processing unit 531 refers to the vapor pressure deficit-$CO_2$ absorption amount correspondence relationship data 526, and calculates the vapor pressure deficit-based estimated value $Pr_{vpd}$ corresponding to the vapor pressure deficit D determined in step S205 (step S206). Note that unlike steps S203 and S204, in step S206, when calculating the vapor pressure deficit-based estimated value $Pr_{vpd}$, the same vapor pressure deficit-$CO_2$ absorption amount correspondence relationship data 526 is used for both plant types 1 and 2.

Next, the estimate processing unit 531 compares the temperature-based estimated value $Pr_{temp}$, the solar radiation amount-based estimated value $Pr_{sr}$, and the vapor pressure deficit-based estimated value $Pr_{vpd}$, and selects the smallest value among the three estimated values as the estimated value, which is then stored in the corresponding column of estimated values of the environmental information table 522 (step S207).

Figure 8:
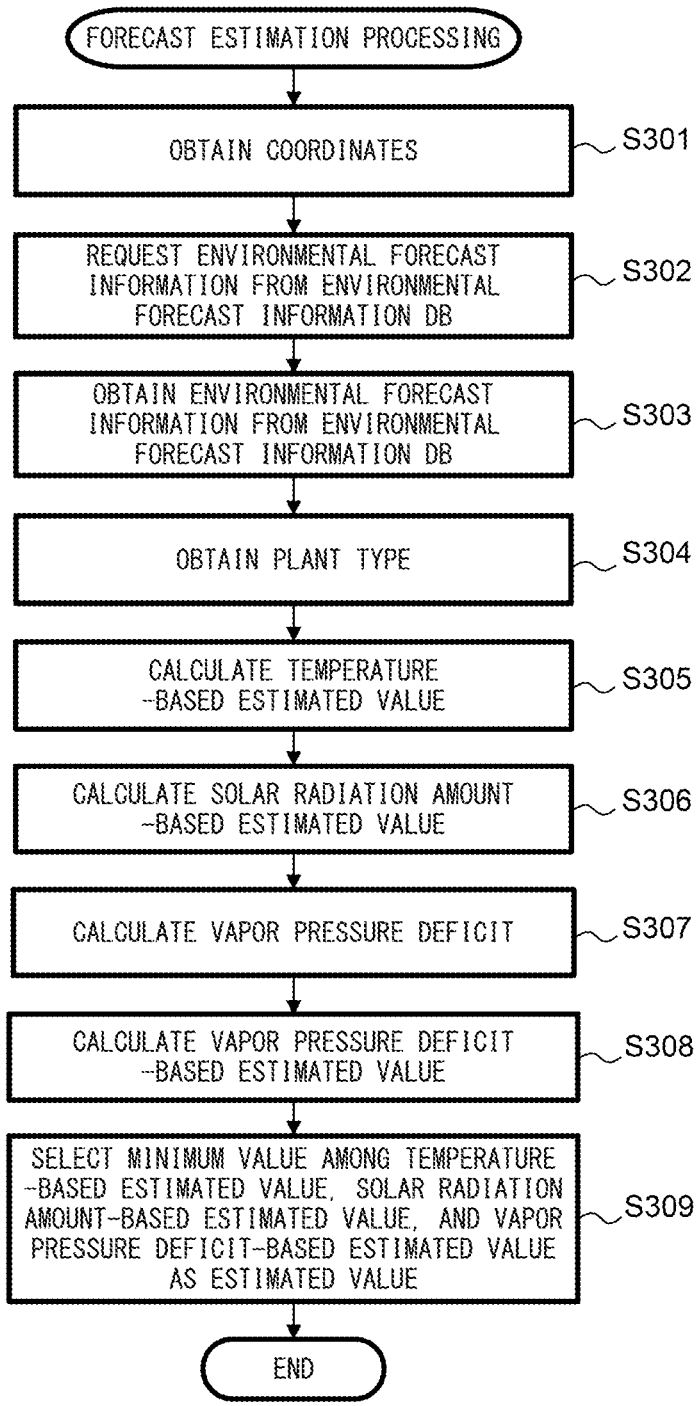
FIG. 8 is a flow chart showing an example of forecast estimation processing.

FIG. 8 is a flowchart showing an example of forecast estimation processing performed by the forecast estimate processing unit 532. The forecast estimate processing unit 532 is executed, for example, on the first day of each month for each sensor terminal 2, and the expected value for the amount of $CO_2$ absorption of the field where the sensor terminal is installed is calculated monthly for, for example, the next four months.

The forecast estimate processing unit 532 selects one sensor ID from the settings table 521 and reads the sensor position corresponding to the selected sensor ID (step S301).

Next, the forecast estimate processing unit 532 accesses the environmental forecast information database 12 using the server communication unit 51, and requests and acquires environmental forecast information at the read sensor location (steps S302, S303). The environmental forecast information includes predicted values of solar radiation amount, air temperature, and relative humidity at the sensor location. Each predicted value for ground surface temperature, solar radiation amount, air temperature, and relative humidity is a month-long average predicted value after one month, two months, three months, and four months. For example, if the current date is March 1st, the average forecast values for the next month are the average values of ground surface temperature, solar radiation amount, air temperature, and relative humidity from April 1st to April 31st. The forecast estimate processing unit 532 stores the acquired environmental forecast information in the forecast table 523. Note that m1, m2, m3, and m4 of forecast months indicate each month after 1 month, 2 months, 3 months, and 4 months, respectively.

Next, the forecast estimate processing unit 532 refers to the settings table 521 and reads the plant type corresponding to the sensor ID selected in step S301 (step S304).

Next, the forecast estimate processing unit 532 refers to the data corresponding to the plant type acquired in step S304 among the ground surface temperature-$CO_2$ absorption amount correspondence relationship data 524, and calculates the temperature-based estimated value $Pr_{temp}$ corresponding to the air temperature included in the environmental forecast information (step S305). Note that this step corresponds to step S203 of the estimation processing executed by the estimate processing unit 531, and though the temperature-based estimated value $Pr_{temp}$ is calculated based on the ground surface temperature in step S203, in step S305, the temperature-based estimated value $Pr_{temp}$ is calculated based on the air temperature instead of the ground surface temperature.

Next, the forecast estimate processing unit 532 refers to the data corresponding to the plant type acquired in step S304 among the solar radiation amount-$CO_2$ absorption amount correspondence relationship data 525, and calculates the solar radiation amount-based estimated value $Pr_{sr}$ corresponding to the solar radiation amount included in the environmental information (step S306).

Next, the forecast estimate processing unit 532 converts the air temperature and relative humidity included in the environmental information using formula (1) above to determine the vapor pressure deficit D (step S307).

Next, the forecast estimate processing unit 532 refers to the vapor pressure deficit-$CO_2$ absorption amount correspondence relationship data 526, and calculates the vapor pressure deficit-based estimated value $Pr_{vpd}$ corresponding to the vapor pressure deficit D determined in step S305 (step S308). Note that unlike steps S305 and S306, in step S308, when calculating the vapor pressure deficit-based estimated value $Pr_{vpd}$, the same vapor pressure deficit-$CO_2$ absorption amount correspondence relationship data 526 is used for both plant types 1 and 2.

Next, the forecast estimate processing unit 532 compares the calculated temperature-based estimated value $Pr_{temp}$, the solar radiation amount-based estimated value $Pr_{sr}$, and the vapor pressure deficit-based estimated value $Pr_{vpd}$, and selects the minimum value among the three estimated values as the estimated value, which is then stored in the corresponding column of the estimated values of the forecast table 523 (step S309).

Figure 9:
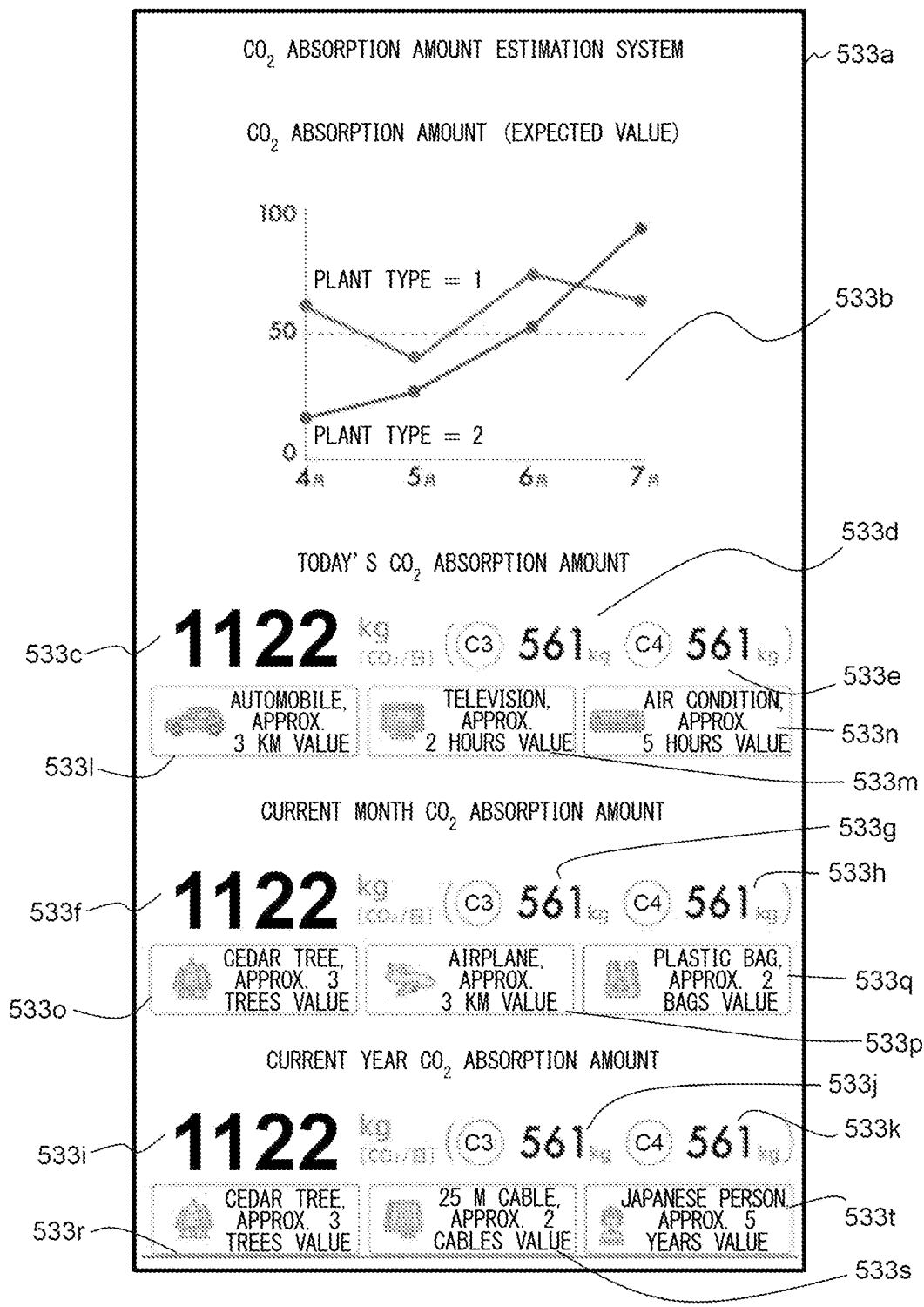
FIG. 9 is a view showing an example of screen display data displayed on a display terminal.

FIG. 9 is a view showing an example of screen display data 533a displayed on the display terminal 4. The numerical values shown in the drawing are numerical values for explaining the screen layout of the screen display data 533a, and do not necessarily match the actual $CO_2$ absorption amounts. Returning to FIG. 4, the screen creation unit 533 creates the screen display data 533a based on the settings table 521, the environmental information table 522, and the forecast table 523.

Graph 533b is a graph of the estimated values of each month after 1 month, 2 months, 3 months, and 4 months determined by forecast estimation processing. The screen creation unit 533 reads the sensor ID whose plant type is 1 based on the settings table 521, and in the forecast table 523, extracts the estimated value of the forecast month m1 for each of the read sensor IDs, and calculates the total value of the estimated values. This calculated value is the predicted value of the $CO_2$ absorption amount that plants of plant type of 1 are expected to absorb during the subsequent one month. The sum of the estimated values for the forecast months m2, m3, and m4 are calculated in the same manner, and the expected values for the months after 2 months, 3 months and 4 months are calculated. By plotting these calculated expected values, the screen creation unit 533 draws a line graph of plant type=1 in the graph 533b. The same applies to the line graph of plant type=2.

The $CO_2$ absorption amount (C3) 533d is a value obtained by the screen creation unit 533 reading the sensor ID whose plant type is 1 (sod C3) from the settings table 521 and integrating, for the read sensor ID, the first estimated value obtained after 0:00 am of the day to the most recently obtained estimated value which are stored in the environmental information table 522.

The $CO_2$ absorption amount (C4) 533e is a value obtained by the screen creation unit 533 reading the sensor ID whose plant type is 2 (sod C4) from the settings table 521 and integrating, for the read sensor ID, the first estimated value obtained after 0:00 am of the day to the most recently obtained estimated value stored in the environmental information table 522.

The total $CO_2$ absorption amount 533c is the sum of the $CO_2$ absorption amount (C3) 533d and the $CO_2$ absorption amount (C4) 533e calculated by the screen creation unit 533.

The index value 533l is a value obtained by the screen creation unit 533 reading the amount of $CO_2$ emitted when a general automobile travels 1 km, which is stored in advance in the server storage unit 52, and dividing the total $CO_2$ absorption amount 533c by this amount.

The index value 533m is a value obtained by the screen creation unit 533 reading the amount of $CO_2$ emitted when an electric power company supplies power required to operate a general television receiver for one hour, which is stored in advance in the server storage unit 52, and dividing the total $CO_2$ absorption amount 533c by this amount.

The index value 533n is a value obtained by the screen creation unit 533 reading the amount of $CO_2$ emitted when an electric power company supplies the power required to operate a general air conditioner for one hour, which is stored in advance in the server storage unit 52, and dividing the total $CO_2$ absorption amount 533c by this amount.

The $CO_2$ absorption amount (C3) 533g is a value obtained by the screen creation unit 533 reading the sensor ID whose plant type is 1 (sod C3) from the settings table 521, in the environmental information table 522, integrating, for the read sensor ID, the first estimated value obtained after 0:00 a.m. up to the estimated value obtained just before midnight on the next day to calculate the $CO_2$ absorption amount per day for each day of the past 30 days, and averaging the $CO_2$ absorption amount per day for the 30 days.

The $CO_2$ absorption amount (C4) 533h is a value obtained by the screen creation unit 533 reading the sensor ID whose plant type is 2 (sod C4) from the settings table 521, in the environmental information table 522, integrating, for the read sensor ID, from the first estimated value obtained after 0:00 a.m. up to the estimated value obtained just before midnight on the next day to calculate the $CO_2$ absorption amount per day for each day of the past 30 days, and averaging the $CO_2$ absorption amount per day for the 30 days.

The total $CO_2$ absorption amount 533f is the sum of the $CO_2$ absorption amount (C3) 533g and the $CO_2$ absorption amount (C4) 533h calculated by the screen creation unit 533.

The index value 533o is a value obtained by the screen creation unit 533 reading the amount of $CO_2$ absorbed by a common Japanese cedar tree in the process of growth, which is stored in advance in the server storage unit 52, and dividing the total $CO_2$ absorption amount 533f by this amount.

The index value 533p is a value obtained by the screen creation unit 533 reading the amount of $CO_2$ emitted when a typical airplane flies 1 km, which is stored in advance in the server storage unit 52, and dividing the total $CO_2$ absorption amount 533f by this amount.

The index value 533q is a value obtained by the screen creation unit 533 reading the amount of $CO_2$ generated when incinerating one general plastic bag, which stored in advance in the server storage unit 52, and dividing the total $CO_2$ absorption amount 533f by this amount.

The $CO_2$ absorption amount (C3) 533j is a value obtained by the screen creation unit 533 reading the sensor ID whose plant type is 1 (sod C3) from the settings table 521, in the environmental information table 522, integrating, for the read sensor ID, the first estimated value obtained after 0:00 a.m. up to the estimated value obtained immediately before midnight on the next day to calculate the $CO_2$ absorption amount per day for each day of the past 365 days, and averaging the $CO_2$ absorption amount per day for 365 days.

The $CO_2$ absorption amount (C4) 533k is a value obtained by the screen creation unit 533 reading the sensor ID whose plant type is 2 (sod C4) from the settings table 521, in the environmental information table 522, integrating, for the read sensor ID, the first estimated value obtained after 0:00 a.m. up to the estimated value obtained immediately before midnight on the next day to calculate the $CO_2$ absorption amount per day for each day of the past 365 days, and averaging the $CO_2$ absorption amount per day for 365 days.

The total $CO_2$ absorption amount 533i is the sum of the $CO_2$ absorption amount (C3) 533j and $CO_2$ absorption amount (C4) 533k calculated by the screen creation unit 533.

The index value 533r is a value obtained by the screen creation unit 533 reading the amount of $CO_2$ that a common Japanese cedar tree absorbs during the growth process, which is stored in advance in the server storage unit 52, and dividing the total $CO_2$ absorption amount 533i by this amount.

The index value 533s is a value obtained by the screen creation unit 533 reading the amount of $CO_2$ when filling a typical 25 m pool at room temperature and one atmosphere, which is stored in advance in the server storage unit 52, and dividing the total $CO_2$ absorption amount 533i by this amount.

The index value 533t is a value obtained by the screen creation unit 533 reading the amount of $CO_2$ that an average Japanese person emits in one year of life, which is stored in advance in the server storage unit 52, and dividing the total $CO_2$ absorption amount 533i by this amount.

According to the present embodiment, the amount of carbon dioxide absorbed by the plants cultivated in a field can be estimated with the same frequency as the measurement of the environmental information based on the environmental information of the field. When determining the estimated value, by determining estimated values based on the ground surface temperature, the solar radiation amount, and the vapor pressure deficit, and adopting the minimum value among them as the estimated value, the estimated value can be obtained by following Liebig's Law of the Minimum. Thus, since the amount of $CO_2$ absorption is estimated based on environmental information which exerts a significant influence when environmental information is measured, a highly accurate estimated value can be obtained as compared to the method of estimating based on a single environmental information.

2. Carbon Dioxide Absorption Estimation System 30

Figure 10:
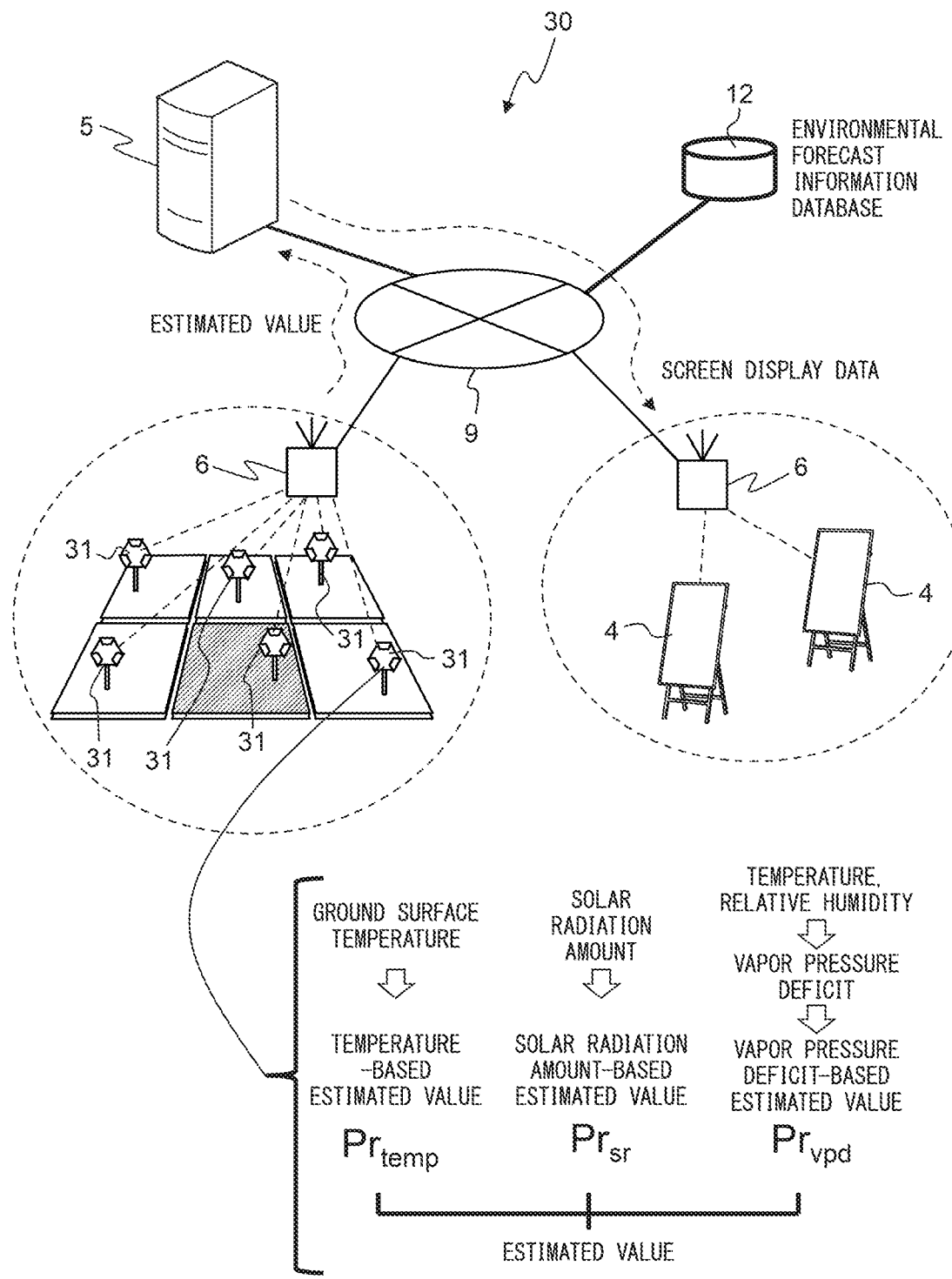
FIG. 10 is a schematic view detailing an overview of a carbon dioxide absorption estimation system according to a second embodiment of the present invention.

FIG. 10 is a schematic view for detailing an outline of another carbon dioxide absorption estimation system 30. Compared with the carbon dioxide absorption estimation system 1 described above, the configuration of the sensor terminal 31 and the operation of the server 5 are partially different. The differences thereof from the carbon dioxide absorption estimation system 1 are described below.

In the carbon dioxide absorption estimation system 30, the sensor terminal 31 installed in each field measures environmental information at regular intervals, and the estimated value of the carbon dioxide absorbed by the plants cultivated in the field where the sensor terminal 31 is installed within that fixed period of time is calculated.

Figure 11:
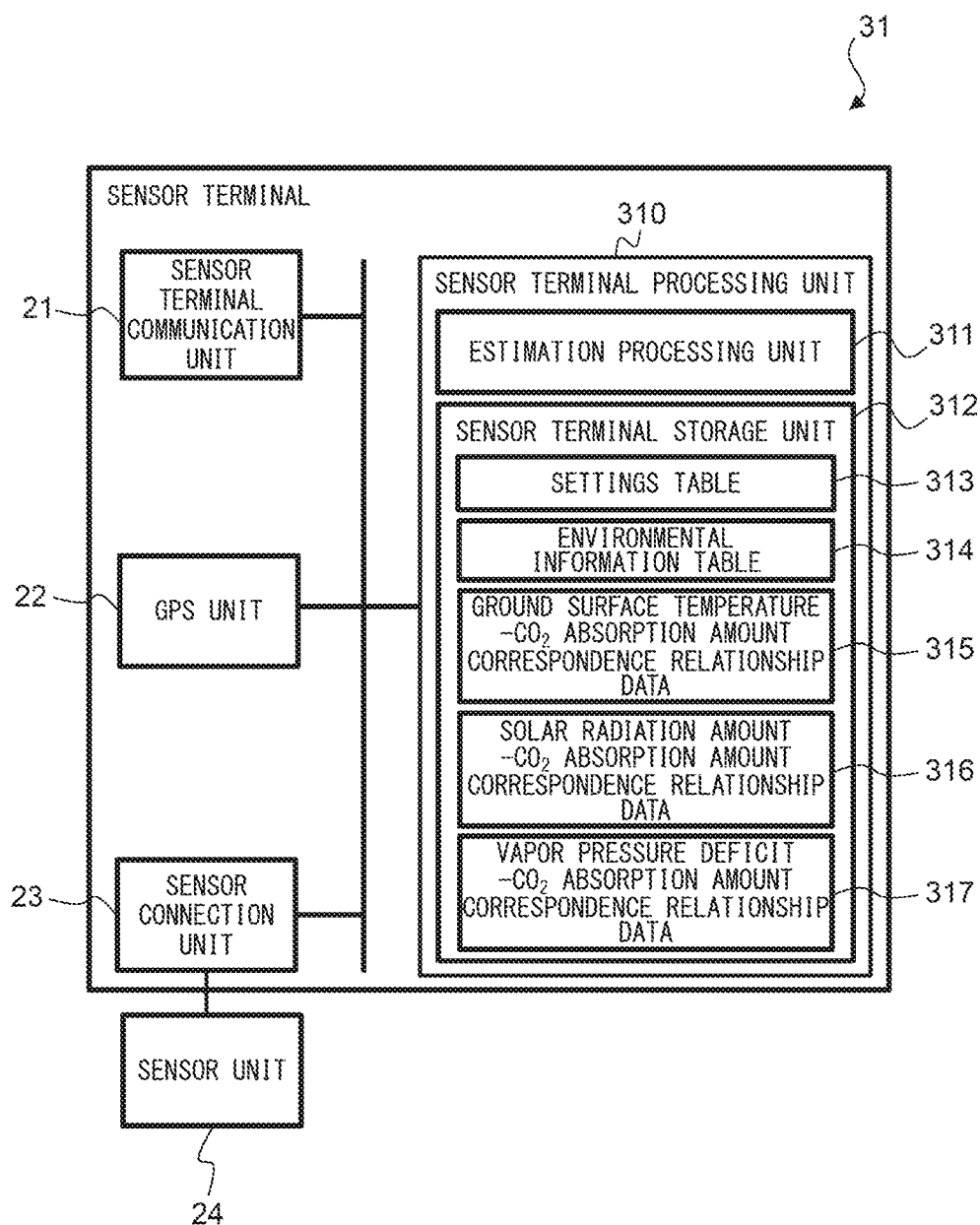
FIG. 11 is a view showing an example of a schematic configuration of a sensor terminal.

FIG. 11 is a view showing an example of the schematic configuration of the sensor terminal 31. Compared with sensor terminal 2 described above, the sensor terminal 31 differs in the configuration of sensor terminal processing unit 310. The sensor terminal processing unit 310 comprises an estimate processing unit 311 and a sensor terminal storage unit 312. The estimate processing unit 311 corresponds to the estimate processing unit 531 of the server 5. The sensor terminal storage unit 312 is an example of a storage unit for storing the correspondence relationships between environmental information and the carbon dioxide ($CO_2$) absorption amounts for the plurality of types of environmental information. The estimate processing unit 311 is an example of a $CO_2$ absorption amount acquisition unit for acquiring a plurality of $CO_2$ absorption amounts by referring to correspondence relationships corresponding to each type of measured environmental information. The estimate processing unit 311 is an example of a minimum value selection unit for comparing a plurality of acquired $CO_2$ absorption amounts and selects the minimum value thereof as the estimated value. The estimate processing unit 311 is an example of a vapor pressure deficit calculation unit which calculates the vapor pressure deficit based on air temperature and relative humidity.

FIG. 12A is a view showing an example of the data structure of a settings table representing the correspondence relationships between sensor ID, sensor position, and plant type, and FIG. 12B is a view showing an example of the data structure of an environmental information table representing the correspondence relationships between measurement time, environmental information, and estimated value. The sensor terminal storage unit 312 stores a settings table 313, an environmental information table 314, ground surface temperature-$CO_2$ absorption amount correspondence relationship data 315, solar radiation amount-$CO_2$ absorption amount correspondence relationship data 316, and vapor pressure deficit-$CO_2$ absorption amount correspondence relationship data 317. The settings table 313 corresponds to the settings table 521 of the server 5. The environmental information table 522 corresponds to the environmental information table 522 of the server 5. Since the ground surface temperature-$CO_2$ absorption amount correspondence relationship data 315, solar radiation amount-$CO_2$ absorption amount correspondence relationship data 316, and vapor pressure deficit-$CO_2$ absorption amount correspondence relationship data 317 are the same as the ground surface temperature-$CO_2$ absorption amount correspondence relationship data 524, the solar radiation amount-$CO_2$ absorption amount correspondence relationship data 525, and the vapor pressure deficit-$CO_2$ absorption amount correspondence relationship data 526 of FIG. 6, illustration thereof has been omitted.

First, the sensor unit 24 connected to the sensor terminal 31 measures environmental information including the air temperature, relative humidity, ground surface temperature, and amount of solar radiation in the field where the sensor terminal 31 is installed at predetermined intervals. The sensor terminal processing unit 310 stores each obtained type of environmental information in the environmental information table 314.

Next, the estimate processing unit 311 executes steps S201 to S207 of FIG. 7 based on the settings table 313 and the environmental information table 314 to calculate estimated values.

Next, the sensor terminal processing unit 310 associates the calculated estimated value, the environmental information used when calculating the estimated value, the measurement time of the environmental information, and the sensor ID of the sensor terminal 31, and transmits them to the server 5 via the base station 6 and the Internet 9.

When the server communication unit 51 receives the estimated value, measurement time, environmental information, and sensor ID, the server processing unit 53 stores the received values in the environmental information table 522. Since the subsequent operations are the same as those of the carbon dioxide absorption estimation system 1 described above, description thereof has been omitted. Note that in the carbon dioxide absorption estimation system 1, the sensor terminal 31 comprises the estimate processing unit 531, and thus, the estimate processing unit 531 of the server 5 may be omitted.

According to the carbon dioxide absorption estimation system 30, the amount of carbon dioxide absorbed by plants cultivated in a field can be estimated based on the environmental information of the field at the same frequency as the measurement of the environmental information in the same manner as the carbon dioxide absorption estimation system 1. A highly accurate estimated value can be obtained as compared to the method of estimating based on a single environmental information.

3. Regarding Modification Examples

The environmental information may further include data representing environmental factors such as soil moisture content, soil electrical conductivity, soil pH, wind direction and speed, vapor pressure deficit, dew point temperature, water level, water temperature, and $CO_2$.

In place of the display terminal, a multifunctional mobile phones (a so-called "smartphone"), mobile information terminal (Personal Digital Assistant. PDA), mobile game machine, mobile music player, tablet PC, mobile phone (a so-called "feature phone") and other mobile terminals may be used. In place of the display terminal, a stationary information processing device such as a desktop computer or workstation may be used.

The measurement cycle for the sensor terminals 2 and 31 for measuring the environmental information may be shorter or longer than 10 minutes, but is preferably 30 minutes or less.

Though the ground surface temperature-$CO_2$ absorption amount correspondence relationship data, solar radiation amount-$CO_2$ absorption amount correspondence relationship data, and vapor pressure deficit-$CO_2$ absorption amount correspondence relationship data are stored as tables in the server storage unit 52 or sensor terminal storage unit 312 in FIG. 6A to C, some or all of these correspondence relationship data may be stored as functions of ground surface temperature/solar radiation amount/vapor pressure deficit and $CO_2$ absorption amount.

Though the estimate processing unit 531 and the estimate processing unit 311 use the vapor pressure deficit-$CO_2$ absorption amount correspondence relationship data which is common between plant types 1 and 2 when calculating the vapor pressure deficit-based estimated value $Pr_{vpd}$, different vapor pressure deficit-$CO_2$ absorption amount correspondence relationship data may be prepared for each type of plant, and the vapor pressure deficit-based estimated value $Pr_{vpd}$. May be calculated in the same manner as calculating the temperature-based estimated value $Pr_{temp}$ and the solar radiation amount-based estimated value $Pr_{sr}$. Further, only one ground surface temperature-$CO_2$ absorption amount correspondence relationship data and solar radiation amount-$CO_2$ absorption amount correspondence relationship data which are common between all plant types may be prepared for calculating the temperature-based estimated value $Pr_{temp}$ and the solar radiation amount-based estimated value $Pr_{sr}$.

It is sufficient that the environmental forecast information include a combination of forecast values from which a temperature-based estimated value, a solar radiation amount-based estimated value, and a vapor pressure deficit-based estimated value can be calculated. For example, when a forecast value for vapor pressure deficit is provided by the environmental forecast information database 12, instead of forecast values for air temperature and relative humidity, the forecast value of the vapor pressure deficit may be acquired from the environmental forecast information database 12, and the acquired vapor pressure deficit may be converted to the vapor pressure deficit-$CO_2$ absorption amount correspondence relationship data 526 to calculate the vapor pressure deficit-based estimated value.

The invention claimed is:

1. A carbon dioxide absorption estimation system comprising a sensor terminal, a server, and an output device,
   wherein the sensor terminal comprises a sensor for measuring a plurality of mutually-differing types of environmental information related to a field provided with the sensor terminal, wherein the environmental information includes ground surface temperature, solar radiation amount, air temperature, and relative humidity,
   wherein the server comprises:
      a storage unit for storing corresponding relationships between respective environmental information and carbon dioxide ($CO_2$) absorption amount for the plurality of types of environmental information;
      a $CO_2$ absorption amount acquisition unit for acquiring a plurality of $CO_2$ absorption amounts with reference to the corresponding relationships corresponding to each type of measured environmental information;
      a minimum value selection unit for comparing the plurality of acquired $CO_2$ absorption amounts and selects a minimum value as an estimated value; and
      a transmission/reception unit for receiving the environmental information from the sensor terminal and transmits information regarding the estimated value to the output device,
   wherein the output device comprises a display unit for displaying the information related to the estimated value,
   wherein the storage unit stores a corresponding relationship defined for each type of plant for a ground surface temperature-$CO_2$ absorption amount corresponding relationship between the ground surface temperature and the $CO_2$ absorption amount and a solar radiation amount-$CO_2$ absorption amount corresponding relationship between the solar radiation amount and the $CO_2$ absorption amount, and
   wherein the $CO_2$ absorption amount acquisition unit references the corresponding relationships in accordance with the plant cultivated in the field where the sensor is installed.

2. The carbon dioxide absorption estimation system according to claim 1, wherein at least one of the sensor terminal and the server has a vapor pressure deficit calculation unit for calculating a vapor pressure deficit based on the air temperature and the relative humidity,
   wherein the storage unit stores the ground surface temperature-$CO_2$ absorption amount corresponding relationship between the ground surface temperature and the $CO_2$ absorption amount, a the solar radiation amount-$CO_2$ absorption amount corresponding relationship between the solar radiation amount and the $CO_2$ absorption amount, and a vapor pressure deficit-$CO_2$ absorption amount corresponding relationship between the vapor pressure deficit and the $CO_2$ absorption amount as the corresponding relationships,
   wherein the $CO_2$ absorption amount acquisition unit acquires a temperature-based estimated value based on the measured ground surface temperature and the ground surface temperature-$CO_2$ absorption amount corresponding relationship, a solar radiation amount-based estimated value based on the measured solar radiation amount and the solar radiation amount-$CO_2$ absorption amount corresponding relationship, and a vapor pressure deficit-based estimated value based on the vapor pressure deficit and the vapor pressure deficit-$CO_2$ absorption amount corresponding relationship as the plurality of $CO_2$ absorption amounts, and wherein the minimum value selection unit selects whichever is least among the temperature-based estimated value, the solar radiation amount-based estimated value, and the vapor pressure deficit-based estimated value as the estimated value.

3. The carbon dioxide absorption estimation system according to claim 1, wherein the sensor measures the plurality of types of environmental information at predetermined time intervals, the $CO_2$ absorption amount acquisition units acquires the plurality of $CO_2$ absorption amounts each time the plurality of types of environmental information are measured, and the minimum value selection unit selects the estimated value each time the plurality of $CO_2$ absorption amounts are acquired.

4. The carbon dioxide absorption estimation system according to claim 3, further comprising an integration unit for integrating the estimated values selected within a predetermined interval.

5. A carbon dioxide absorption estimation system comprising a sensor terminal, a server, and an output device, wherein the sensor terminal comprises:
  a sensor for measuring a plurality of mutually-differing types of environmental information related to a field in which it is installed;
  a storage unit for storing corresponding relationships between respective environmental information and carbon dioxide ($CO_2$) absorption amount for the plurality of types of environmental information;
  a $CO_2$ absorption amount acquisition unit for acquiring a plurality of $CO_2$ absorption amounts with reference to the corresponding relationships corresponding to each type of measured environmental information; and
  a minimum value selection unit for comparing the plurality of acquired $CO_2$ absorption amounts and selects a minimum value as an estimated value, wherein the server comprises a transmission/reception unit for receiving information regarding the estimated value from the sensor terminal and transmits the information regarding the estimated value to the output device, wherein the output device comprises a display unit for displaying the information related to the estimated value, wherein the storage unit stores a corresponding relationship defined for each type of plant for a ground surface temperature-$CO_2$ absorption amount corresponding relationship between a ground surface temperature and the $CO_2$ absorption amount and a solar radiation amount-$CO_2$ absorption amount corresponding relationship between the solar radiation amount and the $CO_2$ absorption amount, and wherein the $CO_2$ absorption amount acquisition unit references the corresponding relationships in accordance with the plant cultivated in the field where the sensor is installed.

6. A carbon dioxide absorption amount estimation method, comprising:
  measuring, by a sensor terminal, a plurality of types of mutually-differing environmental information related to a field provided with a sensor terminal, wherein the environmental information includes ground surface temperature, solar radiation amount, air temperature, and relative humidity;
  receiving, by a server, the plurality of types of environmental information from the sensor terminal;
  referring, by the server, to a corresponding relationship between each of the plurality of types of environmental information and carbon dioxide ($CO_2$) absorption amounts stored in advance in a storage device, for each of the received environmental information to acquire a plurality of $CO_2$ absorption amounts;
  comparing, by the server, the plurality of acquired $CO_2$ absorption amounts with each other and selects a minimum value as an estimated value;
  transmitting, by the server, information regarding the estimated value to an output device;
  displaying, by the output device, the information regarding the estimated value;
  storing, by the server, a corresponding relationship defined for each type of plant for a ground surface temperature-$CO_2$ absorption amount corresponding relationship between the ground surface temperature and the $CO_2$ absorption amount and a solar radiation amount-$CO_2$ absorption amount corresponding relationship between the solar radiation amount and the $CO_2$ absorption amount; and
  referring, by the server, the corresponding relationships in accordance with the plant cultivated in the field where the sensor is installed.

7. A carbon dioxide absorption amount estimation method, comprising:
  obtaining a sensor ID, which is identification information for identifying a sensor terminal, a temperature of a field, solar radiation information regarding an amount of solar radiation emitted onto a field, temperature information regarding a temperature of the field, and humidity information regarding a humidity of the field;
  determining a type of plants cultivated in the field based on the obtained sensor ID;
  calculating vapor pressure deficit information of the field based on the temperature information and the humidity information;
  calculating a temperature-based estimated value based on the temperature information by converting the temperature to temperature-$CO_2$ absorption amount corresponding relationship data of the plant type, a solar radiation amount-based estimated value based on the solar radiation information by converting the solar radiation amount to the solar radiation amount-$CO_2$ absorption amount corresponding relationship data of the plant type, and a vapor pressure deficit-based estimated value based on the vapor pressure deficit information by converting the vapor pressure deficit to the vapor pressure deficit-$CO_2$ absorption amount corresponding relationship data of the plant type, which are estimated values of an absorption amount of carbon dioxide per unit time of the field; and
  selecting a minimum value obtained by comparing the temperature-based estimated value, the solar radiation amount-based estimated value, and the vapor pressure deficit-based estimated value with each other as an estimated value of the absorption amount of carbon dioxide of the field.

* * * * *